United States Patent [19]

Loos

[11] 4,245,909

[45] Jan. 20, 1981

[54] OPTICAL INSTRUMENT FOR MEASUREMENT OF PARTICLE SIZE DISTRIBUTIONS

[76] Inventor: Hendricus G. Loos, 3019 Cresta Way, Laguna Beach, Calif. 92651

[21] Appl. No.: 919,281

[22] Filed: Jun. 26, 1978

[51] Int. Cl.³ .............................................. G01N 15/02
[52] U.S. Cl. .................................... 356/336; 250/574; 350/162 SF
[58] Field of Search ...................... 356/336, 340, 342; 250/574; 350/162 SF

[56] References Cited

U.S. PATENT DOCUMENTS

| | | | |
|---|---|---|---|
| 3,469,921 | 9/1969 | Taylor | 356/335 |
| 3,873,206 | 3/1975 | Wilcock | 356/336 X |
| 4,037,965 | 7/1977 | Weiss | 356/336 |
| 4,052,600 | 10/1977 | Wertheimer | 356/336 X |

OTHER PUBLICATIONS

Malvern Instrument Ltd. Division of Precision Devices and Systems, Malvern, Worcestershire, England, "Particle and Droplet Size Distribution Analyzer Type ST 1800".

*Primary Examiner*—John K. Corbin
*Assistant Examiner*—Bruce Y. Arnold
*Attorney, Agent, or Firm*—Donald D. Mon

[57] ABSTRACT

A method for measurement of the size distribution of particles suspended in a gas or in a liquid. The particle suspension is illuminated by a collimated beam of nearly monochromatic light. Part of the light scattered by the particles is collected by a lens and is passed through a spatial filter placed in the focal plane of the lens. The light transmitted by the filter is measured by a photodetector. The photodetector output is measured as different spatial filters are switched in place. A computer, microprocessor, or analog device acts on the measured values and produces the particle size distribution as an output. The data reduction algorithm consists of a linear transformation of the measured data vector, followed by the construction of a linear combination of basis functions for the size distribution. The spatial filters consist of transparencies with non-uniform transmittance functions. The average scattering angle is not restricted, but for broad polydisperse particle distributions near back scatter is preferred, in order to avoid an ill-conditioned data reduction problem. One of the spatial filters has a uniform transmittance for the purpose of background light subtraction, and to provide a bias in order to allow effectively indefinite filter transmittance functions.

47 Claims, 7 Drawing Figures

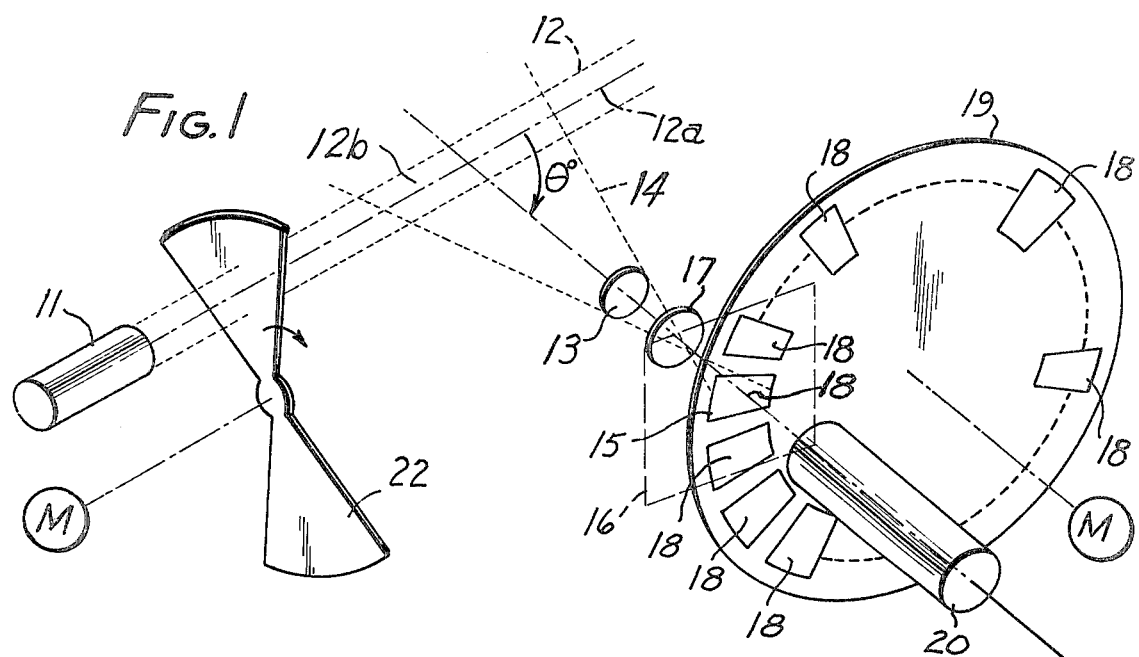
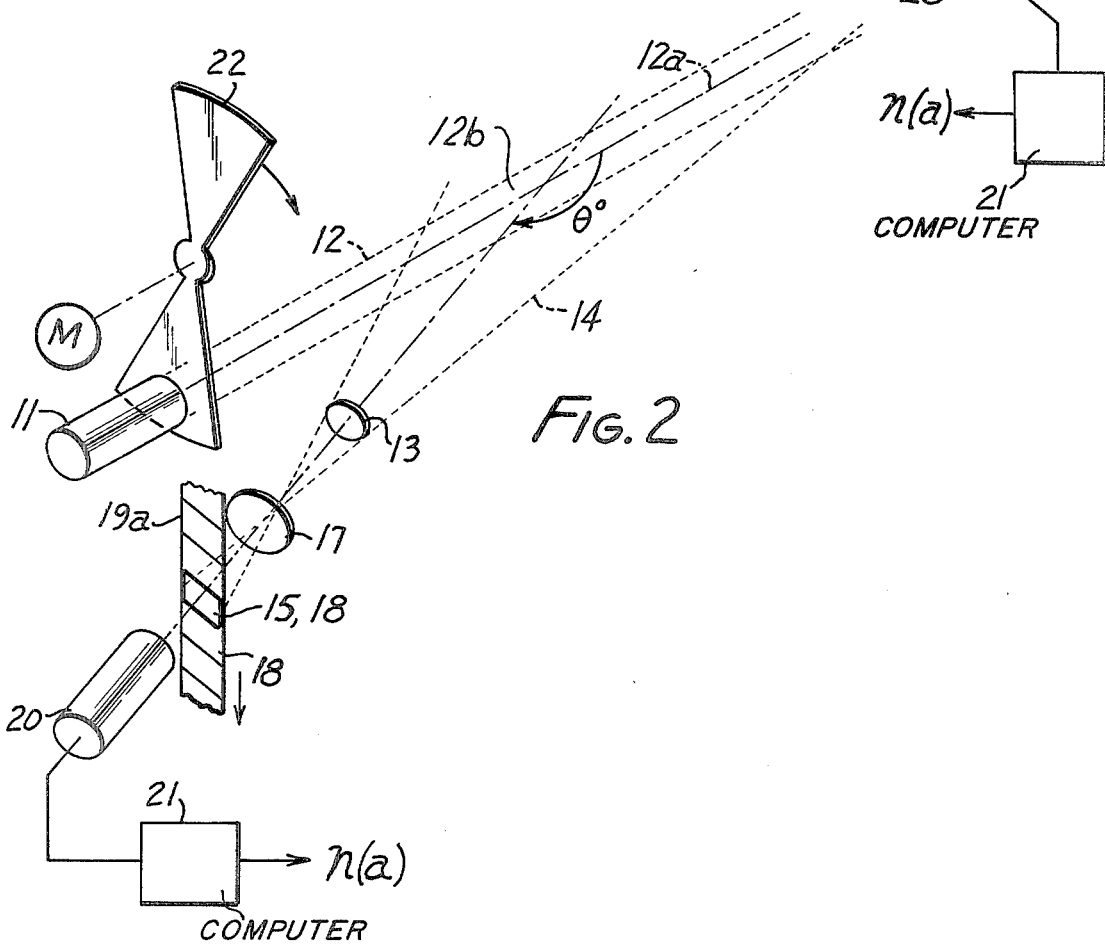

OPTICAL INSTRUMENT FOR MEASUREMENT OF PARTICLE SIZE DISTRIBUTIONS

This invention was made prior to and during the course of work performed under a contract with the Office of Naval Research.

The invention pertains to the rapid measurement of the size distribution of particles suspended in a gas or in a liquid. For simplicity the discussion in the present section is made to refer to the case of water drops suspended in air. In most of the known instruments which are presently available for measurement of drop size distributions, sample air is moved through a small highly illuminated volume of space, and light scattered by the individual drops, as they move in single file through this volume, is measured by a photodetector. The drop size is determined from the intensity of the electric pulse out of the photodetector. This method suffers from a number of deficiences, notably the edge effect, the velocity effect, and counter swamping. The edge effect arises because drops which pass through the scattering volume near the edge of the illuminating beam are illuminated less and therefore scatter less light. This causes the instrument to undersize the drop. The velocity effect arises in airborne applications, where the cloud drops move rapidly through the scattering volume. The resulting short detector pulse duration requires somewhat different electronics parameters than those used for terrestrial laboratory work, where the drop velocity is small. As a consequence, laboratory calibration of the instrument, unless it is done in a wind-tunnel, is of limited utility for airborne measurements. Counter swamping may occur when drop size distributions are measured in dense clouds aboard a fast flying aircraft.

The measurement method comprised in the present invention suffers from none of the deficiencies discussed. Instead of counting and sizing individual scattering events, the instrument looks at a sizeable volume of cloud (from about one liter to several cubic meters) and it processes the light scattered from all drops in this volume collectively. This makes it possible to measure drop size distributions in clouds, fogs, or in laboratory cloud chambers in situ, without disturbing the cloud. Furthermore, it becomes possible to perform bulk measurements, in which average drop size distributions in a large volume are determined rapidly.

In practice, the light scattered by the multitude of individual particles adds incoherently. In the case of spherical particles, each particle scatters light in its characteristic Mie intensity pattern; these Mie patterns superimpose and give rise to a scattered light intensity which is a certain function of scattering angle. It is the object of the present invention to provide a means for determining the particle size distribution from this scattered light function.

Under circumstances often encountered, the conversion from the scattered light function to the particle size distribution constitutes an ill-conditioned data reduction problem, which results in low instrument accuracy. It is a further object of the present invention to circumvent this problem.

The measurement of the scattered light function may be done by means of an array of photodetectors, as in the apparatus of Malvern Instrument, Ltd., of Malvern Worcestershire, England. This requires the photodetectors to be small solid state devices, such as photodiodes, and this restricts the detection performance of the instrument such that only relatively dense particle suspensions can be measured accurately. Using photomultiplier tubes instead of photodiodes would result in a much increased instrument sensitivity, but use of an array of photomultiplier tubes would be prohibitive in cost and size. Therefore, there is merit in a method which requires only a single photodetector for the measurement of light scattered by the particles. For this photodetector, a photomultiplier tube can then be used.

It is a further object of the present invention to determine the particle size distribution by using a single photodetector for the measurement of the light scattered by the particles.

There are several situations in which it is desirable to utilize scattering angles near 180°, i.e., near backscattering. Such an arrangement makes it possible to have the light source and detector in the same general location, and yet measure particle size distributions in a large volume or at rather large distances from the apparatus. It is a further object of the present invention to provide a method for determining particle size distributions which can be used with near backscattered light.

Often, there is undesirable background light in the form of daylight, or from light sources extraneous to the instrument. In cloud chamber work, the illuminated cloud drops inside the chamber scatter light in all directions; some of this light is reflected by or scattered off the chamber walls, and this results in undesirable background light which enters the instrument. It is a further object of the present invention to provide means to effectively subtract background light in the instrument process.

It is yet another object of the present invention to provide a means of measuring particle size distributions in real time.

By way of summary, the objects of the invention are achieved by passing a collimated beam of nearly monochromatic polarized light through the particle suspension and by collecting part of the light scattered by the particles located in a portion of the illuminating beam by a photodetector, after the light has passed through a lens and through a spatial filter placed in the focal plane of the lens. Different spatial filters are brought into position behind the lens in quick succession, and the sequence of measured photodetector outputs is acted upon by a linear transformation, followed by the formation of a linear combination of basis functions for the particle size distribution, executed by a computer, microprocessor, or an analog device.

The invention will be fully understood from the following detailed description and the accompanying drawings, in which:

FIG. 1 shows one arrangement of the invention, in which a disc is used for mounting and switching a plurality of spatial filters;

FIG. 2 shows the presently preferred embodiment, employing near backscattering, and a film strip for switching a plurality of spatial filters.

Figure 3:
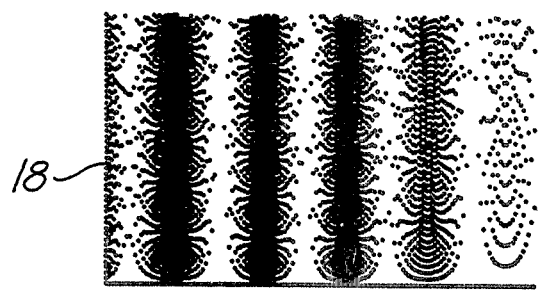
FIGS. 3-7 are plan views of transparencies bearing patterns which form spatial filters.

Referring now to FIG. 1, a light source 11 produces a collimated or nearly collimated beam 12 of nearly-monochromatic polarized light, which illuminates the particle suspension. A lens or lens system 13, whose optical axis makes an angle $\theta$ with the principal direction 12$a$ of beam 12, processes light scattered by the particles located in the volume 12$b$ of the beam 12 inside the cone 14, the latter constituting the field of view of an optical configuration consisting of lens 13 and an image window 15, located in the focal plane 16 of lens 13.

In this specification, the term "focal plane" is defined as the plane which sharply images objects at infinity.

A polarizing element 17 is placed in the path of scattered light, preferably but not necessarily between the lens 13 and image window 15. A perfect lens 13 would map incoming light rays located inside cone 14 onto points in image window 15. Therefore, part of the light scattered by an angle $\theta$ by all particles in the volume 12b is imaged onto a curve in window 15. As a consequence, for spherical and monodispersed particles, the light intensity in image window 15 will be distributed according to a Mie intensity pattern.

A set of (N+1) spatial filters 18 is mounted on a disc 19 in plane 16. Arrangements are made such that, in time, different spatial filters are switched into the position of window 15.

An alternate embodiment of the switching concept consists of a filmstrip 19a, the frames of which are the individual spatial filters. The filmstrip is moved past the window in step-wise motion-picture fashion. The filmstrip (FIG. 2) can be looped, without beginning or end, if preferred.

There is the option of chopping the beam 12 of light by a chopper 22, and using synchronous detection in a manner which will be evident to those skilled in the art.

There is the further option of having either disc or filmstrip move continuously, and to flash the light source 11 synchronously with the filter position. A gated amplifier or integrator can then be used in the signal processing.

Each spatial filter consists of a transparency, the transmittance of which is a function of location on the transparency. Behind the image window 15 and the spatial filter 18 there is a photodetector 20, which is usually a photomultiplier tube. With the $i^{th}$ spatial filter in place, the signal from the photodetector 20, usually after amplification and integration, (possibly gated), is measured and serves as input $s_i$ for a computer 21. In the present context, the computer 21 may be a computer, a microprocessor, or an analog device, such as a CCD or CTD. There are N+1 different spatial filters on the disc 19, and hence, there are N+1 signals $s_j$. The computer 21 is programmed or arranged such as to execute a linear transformation of the data sequence $s_i$, i=0,1, ... N, by means of a matrix $T_{ij}$, which is present in the computer, or embodied in an analog device, in a manner as will be evident to those skilled in the art. The result of this linear transformation is the sequence $$b_j = \sum_{i=0}^{N} T_{ij} s_i, \quad (1)$$

j=1, ... N. As a further action of the computer, the sum $$n(a) = \sum_{j=1}^{N} b_j n_j(a) \quad (2)$$

is computed, where the $n_j(a)$ are N basis functions for the particle size distribution function, a being the particle radius, or some other particle size characterizing number. The function n(a) is the particle size distribution which is the object of the measurement. It may be displayed, printed, or used as input for further calculations in a manner evident to those skilled in the art. The number $b_o$ is not used in the particle size distribution calculation (2), since things are arranged such that $b_o$ is a measure of the background light, and such that the $b_j$, j=1, ... N, are not influenced by the background light. Essential to this arrangement is the use of one spatial filter, say with j=0, which has uniform transmittance.

The action of the filters may be understood as follows. Suppose that the cloud consists of drops of a uniform size. If for that case the filter 18 in the image window 15 would be replaced by a screen, the light processed by the apparatus would illuminate this screen with a non uniform intensity, showing light and dark bands, which are called a Mie pattern. The Mie pattern depends on the angle $\theta_o$ between the optical axis of the lens and the beam direction, as well as on the field of view of the cone 14, and it also depends on the size and the refractive index of the scattering cloud drops. If now different filters are switched into place, maximum light would get passed by a filter which has a transmittance pattern which precisely matches the MIE pattern of the incoming light. In this manner, the Mie pattern of the light coming into the window 15 is recognized, and the drop size is inferred. For a cloud with a mixture of drop sizes, the algorithym discussed unravels the separate contributions by the Mie patterns belonging to the different drop sizes to the total light intensity distribution in the window. It is possible to use filter transmittance distributions other than Mie patterns belonging to single drop sizes, by taking linear combinations of such Mie patterns for different sizes.

In order to enable those skilled in the art to construct the proper transmittance functions for the spatial filters 18, the following discussion is presented, in which square integrable functions are considered as vectors in a Hilbert space H. Let $\vec{n}$ denote the vector of the particle size distribution n(a), and let $\vec{v}$ denote the vector of the light intensity distribution of the scattered light incident on the image window 15. Since in practical cases the light scattered by the individual particles adds incoherently, one has $$\vec{v} = M\vec{n}. \quad (3)$$

where M is a linear operator on H, which may be thought of as an infinite dimensional matrix. If M is non singular, one has $$\vec{n} = M^{-1}\vec{v}, \quad (4)$$

where $M^{-1}$ is the inverse of M. In practice, measurement of $\vec{v}$ contains noise $\Delta\vec{v}$, which results in a noise part $$\Delta\vec{n} = M^{-1}\Delta\vec{v} \quad (5)$$

in the measured particle size distribution. From (4) and (5) one has $$\frac{|\Delta\vec{n}|}{|\Delta\vec{n}|} = \frac{|M^{-1}\Delta\vec{v}|}{|M^{-1}\vec{v}|} = \frac{|M^{-1}\Delta\vec{v}|}{|M^{-1}\vec{v}|} \Big/ \frac{|\Delta\vec{v}|}{|\vec{v}|}.$$

-continued $$\frac{\left\|\overrightarrow{\Delta v}\right\|}{\left\|\overrightarrow{v}\right\|} = \frac{\left\|M\overrightarrow{n}\right\|/\left\|\overrightarrow{n}\right\|}{\left\|M\overrightarrow{\Delta n}\right\|/\left\|\overrightarrow{M\Delta n}\right\|} \cdot \frac{\left\|\overrightarrow{\Delta v}\right\|}{\left\|\overrightarrow{v}\right\|},$$

where { { denotes the Euclidean norm (see, for instance, W. Schmeidler, "Linear Operators in Hilbert Space", Academic Press, New York, 1965, pages 10 and 13). Therefore, the inverse map (4) brings about a signal to noise ratio degradation $$\beta = \frac{\max\left(\left\|M\overrightarrow{n}\right\|/\left\|\overrightarrow{n}\right\|\right)}{\min\left(\left\|M\overrightarrow{\Delta n}\right\|//\left\|\overrightarrow{\Delta n}\right\|\right)}, \tag{6}$$

where the maximum is taken over non-negative functions $\overrightarrow{n}$, and the minimum is taken over functions $\Delta\overrightarrow{n}$ which have no definiteness restriction. In (6), the vectors $\overrightarrow{n}$ and $\Delta\overrightarrow{n}$ over which the maximum and minimum are taken may be restricted to a subspace S of H. Then, $\beta$ depends on the subspace S, and, of course, on the scattering angle interval comprized by the field of view cone 14. If $\beta_o$ is an acceptable value for the degradation of the inverse map (4), a subspace S of H is called good if $\beta \leq \beta_o$. The data reduction method outlined amounts to approximating particle size distributions as vectors in a good subspace G. The utility of this procedure depends on whether in practice particle distributions and their differences have negligible components in the orthogonal compliment B of G. Calculations have shown that for waterdrops in air, and for scattering angle ranges away from near-forward or near backward directions, the subspace B contains vectors $\Delta\overrightarrow{n}$ which can occur in practice as the difference between broad polydispersed drop size distributions. This is because in the Mie intensity pattern for monodispersed waterdrops in air the maxima and minima in the region away from the near forward and near backward directions shift very rapidly with changing scattering parameter $\alpha = 2\pi a/\lambda$ (a is the drop radius, and $\lambda$ is the light wavelength), whereas the distance between consecutive maxima varies slowly with $\alpha$. Hence, if one adds the Mie patterns of two drops of slightly different sizes, the maxima and minima fill in, thereby diminishing the norm of the ac component of $\overrightarrow{v}$. It follows that an instrument designed for a scattering angle range away from the near-forward or near-backward directions is only suitable to measure rather monodisperse drop size distributions. For accurate measurement of broad polydisperse drop size distribution one must use near-forward or near backward scattering as in FIG. 2. This is because for varying $\alpha$ the scattering intensity versus scattering angle $\theta$ always has a maximum at $\theta = 0$, and either a maximum or a minimum at $\theta = 180°$. Therefore, the "phase" of the Mie "waves" is locked in at $\theta = 0°$, and at $\theta = 180°$ (up to a flip of $\pi$), so that, near these angles, the maxima and minima do not change position so rapidly as function of $\alpha$. Furthermore, computer studies have shown that the near-backscatter range is more suitable for the accurate measurement of broad polydispersed drop size distributions, if Gaussians with a relative standard deviation of about 10% are used as basis functions, in a manner described below. Let the N linearly independent basis functions $\overrightarrow{n}_i$, $i=1, \ldots N$, belong to the good subspace G. We approximate the particle size distribution as a linear combination $$\overrightarrow{n} = \sum_{i=1}^{N} b_i \overrightarrow{n}_i. \tag{7}$$

With $$\overrightarrow{v}_i = M\overrightarrow{n}_i \tag{8}$$

one has $$\overrightarrow{v} = \sum_{i=1}^{N} b_i \overrightarrow{v}_i. \tag{9}$$

A solution for $b_i$ may be obtained by forming the scalar products (correlations).

$$\overrightarrow{v} \cdot \overrightarrow{v}_j = \sum_{i=1}^{N} b_i C_{ij}, \tag{10}$$

where $$C_{ij} = \overrightarrow{v}_i \cdot \overrightarrow{v}_j. \tag{11}$$

One then has $$b_i = \sum_{j=1}^{N} C_{ij}^{-1} \left(\overrightarrow{v} \cdot \overrightarrow{v}_j\right). \tag{12}$$

where $C_{ij}^{-1}$ is the inverse of $C_{ij}$. The particle size distribution is found from $$\overrightarrow{n} = \sum_{i,j=1}^{N} C_{ij}^{-1} \left(\overrightarrow{v} \cdot \overrightarrow{v}_j\right) \overrightarrow{n}_i. \tag{13}$$

The correlation $\overrightarrow{v} \cdot \overrightarrow{v}_j$ is implemented in the present invention by passing the scattered light through lens 13 and through the $j^{th}$ spatial filter 18 with transmittance $\overrightarrow{v}_j$ in focal plane 16 of lens 13. The light incident on the filter has the intensity distribution $\overrightarrow{v}$. The total light intensity transmitted by the filter is $\overrightarrow{v} \cdot \overrightarrow{v}_j$. $C_{ij}^{-1}$ is essentially the instrument matrix $T_{ij}$ of (1); further discussion clarifying the role of $i=0$ or $j=0$ follows.

Since the basis functions $\overrightarrow{n}_j$ lie in the good subspace G, they can be chosen such that the matrix is far from singular, and the matrix multiplication (13) does not give rise to a large degradation of signal to noise ratio. (12) written in the form $$b_i = \overrightarrow{v} \cdot \left(\sum_{j=1}^{N} C_{ij}^{-1} \overrightarrow{v}_j\right) \tag{14}$$

shows that the linear transformation can be absorbed in the optical process, by taking spatial filters with transmittance functions $$\sum_{j=1}^{N} C_{ij}^{-1} \overrightarrow{v}_j.$$

Resulting negative transmittance can be embodied in practice by using a bias to raise all filter transmittances to non-negative values, and by adding an (N+1) st filter (j=0) with a uniform transmittance. This filter can also be used to achieve subtraction of background light, by considering the uniform function $\bar{n}_o$ as the density of a "dummy" scattering object, which gives a scattering function $\bar{v}_o$ equal to the background light contribution to $\bar{v}$. Including the dummy scatterer in (7) gives $$\vec{n} = \sum_{i=0}^{N} b_i \vec{n_i}. \tag{15}$$

and extending the range of j in (12) gives $$b_i = \sum_{j=0}^{N} C_{ij}^{-1} \left( \vec{v} \cdot \vec{v_j} \right), i = 1, \ldots N. \tag{16}$$

where now, $C_{ij}^{-1}$ is the inverse of the N+1 dimensional matrix $C_{ij}$. The $b_i$, i=1, ... N, of (16) are not influenced by the background light. The inclusion of the linear transformation in the optical process, and the biasing of the filter transmittances to non-negative values may be done as follows. Inclusion of j=0 in (14) gives $$b_i = \vec{v} \cdot \left( \sum_{j=0}^{N} C_{ij}^{-1} \vec{v_j} \right), i = 1, \ldots N. \tag{17}$$

Let $C_i$ be a positive number such that none of the functions $$a_i \vec{g_i} = \sum_{j=0}^{N} C_{ij}^{-1} \vec{v_j} + C_i \vec{v_c}, i = 1, \ldots N. \tag{18}$$

attains negative values anywhere on the window 15. Then, with $a_i = \max \bar{g_i}$, the functions $\bar{g_i}$, i=1, ... N, are implementable as transmittance functions of the filters i=1, ... N. (17) may be written $$b_i = a_i \vec{v} \cdot \vec{g_i} - c_i (\vec{v} \cdot \vec{v_o}), i=1, \ldots N. \tag{19}$$

If $s_i$ is the photodetector signal with the ith filter in position, (19) may be written $$b_i = a_i s_i - C_i S_o, i=1, \ldots N. \tag{20}$$

Hence, this embodiment gives a shorter computer calculation of the coefficients $b_i$ of expansion of the particle size distribution n(a) in terms of the basis functions $n_i(a)$, i=1, ... N.

It will be evident to those skilled in the art how to apply this procedure to the case in which the background light illuminates window 15 in a non-uniform manner, and a $0^{th}$ filter with an appropriate non-uniform transmittance is used for the implementation of indefinite filter transmittances. The description above has been given in terms of water drops in air. It applies as well to other spherically symmetric particles, suspended in a gas or a liquid except that certain ratios of refractive index of the particles and the suspending medium may favor near forward scattering rather than near backscattering. In such cases, the angle $\theta_o$ must be appropriately adjusted, but the method of measurement and data reduction remains the same. The method also applies to the case of non-spherically symmetric particles suspended in a gas or liquid, possibly with some degradation of performance of the instrument. The particles may be biological cells, bacteria, or other biological organisms, and the invention may be used to determine the concentrations of the various species of cells, bacteria, organisms, or particles which are present in a sample. The particles may be suspended on a transparent slide which is illuminated by the light beam, instead of being suspended by a gas or a liquid in the bulk.

There are various options concerning the polarization of the beam 12, and the polarizing element 17, as follows. The instrument will work with an unpolarized light source 11, and without the polarizing element 17. In fact, this is the preferred polarization mode for very near forward scattering or very near backscattering, i.e., where the intensities of the scattered light in both polarized directions are substantially the same. For $\theta_o$ not very close to 0° or 180°, an improvement in instrument performance is achieved by using a light source 11 which is polarized (E direction) perpendicular to the plane P through the illuminating beam axis and the optical axis of the lens. The use of a polarizing element 17 is then optional; if used, the polarization direction should be perpendicular to the plane P. As an alternative, an unpolarized light source 11 can be used, together with a polarization element 17, polarized perpendicular to the plane P. As a further alternative, the light source 11 may be polarized in the direction of P, and there is then again the option of using a polarizing element 17; if used, the element 17 should be polarized in the direction of P. As a further alternative, an unpolarized light source may be used, with element 17 polarized in the direction of P.

The preferred embodiment of the invention and its best mode for use in clouds or fogs is shown in FIG. 2. In this case, near backscattering is used, making it possible to have light source 11 and detector unit close together while sampling a substantial volume of cloud or fog. The element numbers are the same as in FIG. 1, with the exception of the embodiment of the set of filters, which now is in the form of a filmstrip 19a looped and therefore without end. It is important that either the illuminating light intensity in beam 12 is very nearly the same from frame to frame exposure of the filmstrip, or else that the variation of this light intensity is measured accurately. It will be evident to those skilled in the art how to achieve this objective, if necessary by the use of an auxiliary photodetector which measures the illuminating light intensity.

Figure 4:
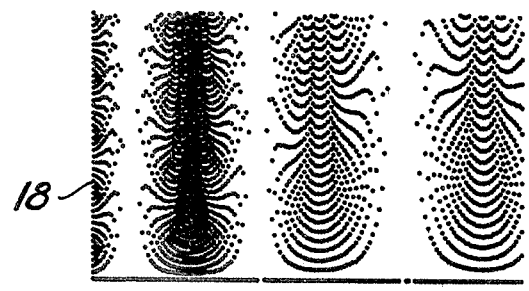
Figure 5:
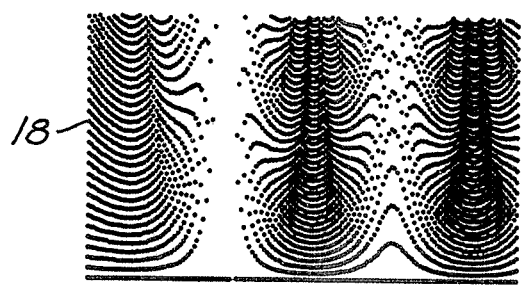
Figure 6:
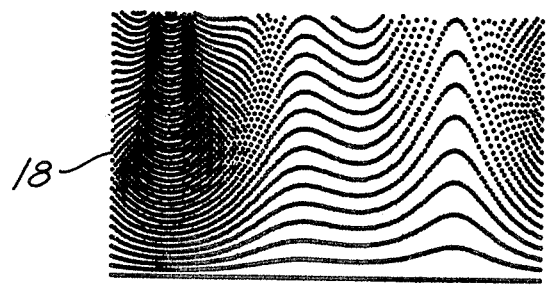
Figure 7:
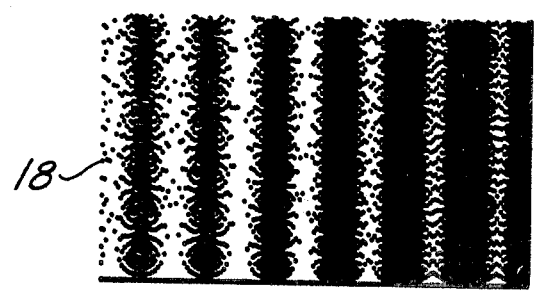

FIGS. 3-7 show examples of negatives of transmittance functions for spatial filters for use in FIG. 1 with $\theta_o = 90°$. These functions have been generated by a computer-driven plotter, from a calculation of Mie intensities for water drops in air. In these plots, the dot density along vertical lines is proportional to the average filter transmittance along vertical lines. In this particular example, the angle $\theta_o$ is 90°, and the coarse-grained average filter transmittance is approximately constant along vertical lines. For angles $\theta_o$ different from 90°, the filter transmittance is constant along curves which are conical sections of constant scattering angle $\theta$.

Another method for the construction of the filters consists of making a picture in the form of a slide, of a semi-transparent sheet assembly, which is illuminated from the opposite side of the camera, where the sheet assembly consists of strips of semi-transparent material such as paper, put together in layers in such a manner as to produce an assembly with the desired transmittance pattern.

Yet another method for the construction of the filters consists of producing a cloud with uniform drop size, or with a certain desired drop size distribution, and using a camera instead of the assembly 13, 18, 19 and 20, in such a manner that the camera lens is identical to the lens 13, and is placed in the position of lens 13 and such that the camera film window coincides with the image window 15. Using the proper exposure time, the picture produced in this manner, in the form of a slide, will have the proper transmittance pattern. A preferred method for the construction of the filters consists of controlling a camera orientation by means of two computer-driven angular positioners, and illuminating the camera lens with a fixed collimated light beam, which passes through a computer-controlled shutter. Alternatively, the intensity of the light beam may be modulated by the computer.

When a polarizing element is placed in the path of the scattered light, it may be placed on either side of the lens, preferably ahead of the spatial filter.

Chopping or flashing the light source is useful but not essential. A steady light source can be used. However, significant advantages are obtained by providing light intermittently, for example improvement in the signal to noise ratio, discrimination against background light, and discrimination against dc input voltage drift of the amplifiers behind the photodetector.

This invention is not to be limited by the embodiments shown in the drawings and described in the description, which are given by way of example and not of limitation, but only in accordance with the scope of the appended claims.

What is claimed is:

1. A method for measurement of the size distribution of particles suspended in a gas or a liquid, comprising:
    passing a substantially collimated beam of substantially monochromatic light into the particle suspension, said beam having a beam axis;
    with a lens collecting part of the light scattered by the particles, the optical axis of said lens making a non-zero angle with the axis of the illuminating beam;
    sequentially placing the members of a set of spatial filters in an image window located in the focal plane of said lens;
    collecting the light transmitted by each of said spatial filters sequentially by a photodetector to produce a signal substantially proportional to light transmitted by respective filters;
    acting on the resulting photodetector signal sequence by a linear transformation; and
    using the resulting data sequence as coefficients in a linear combination of basis functions to yield the particle size distribution.

2. A method according to claim 1 in which the filter set is carried by a rotating disc.

3. A method according to claim 2 in which said disc moves continuously, and the light source is flashed when a member of the set of spatial filters is aligned with said image window.

4. A method according to claim 1 in which the filter set comprises a filmstrip.

5. A method according to claim 4 in which the filmstrip moves continuously, and the light source is flashed when a member of the set of spatial filters is aligned with said image window.

6. A method according to claim 1 in which the filters are transparencies with a non-uniform transmittance, which at any point P of the filter is a function of the angle $\theta$ which rays that have P as an image make with the axis of the illuminating beam.

7. A method according to claim 6 in which the filter transmittance is computer generated from Mie intensity scattering calculations.

8. A method according to claim 1 in which one of the filters of the set has a uniform transmittance.

9. A method according to claim 8 in which said uniform transmittance filter is used for subtraction of background light.

10. A method according to claim 1 in which the collected scattering angle range is near backward scattering.

11. A method according to claim 1 in which said linear transformation and the said linear combination are performed by microprocessor.

12. A method according to claim 1 in which said linear transformation and the said linear combination are performed by an analog device.

13. A method according to claim 1 in which a polarizing element is placed in the path of the said scattered light.

14. A method according to claim 13 in which the polarizing element is placed ahead of the spatial filters.

15. A method according to claim 1 in which a light chopper is placed in the illuminating beam.

16. A method according to claim 15 in which synchronous detection is used for the photodetector signal.

17. A method according to claim 1 in which a filter with non-uniform transmittance is provided in said set to be used for subtraction of background light.

18. A method according to claim 1 in which said beam is polarized.

19. A method according to claim 18 in which the filter set is carried by a rotating disc.

20. A method according to claim 19 in which said disc moves continuously, and the light source is flashed when a member of the set of spatial filters is aligned with said image window.

21. A method according to claim 18 in which the filter set comprises a filmstrip.

22. A method according to claim 21 in which the filmstrip moves continuously, and the light source is flashed when a member of the set of spatial filters is aligned with said image window.

23. A method according to claim 18 in which the filters are transparencies with a non-uniform transmittance, which at any point P of the filter is a function of the angle $\theta$ which rays that pass through the point P make with the axis of the illuminating beam.

24. A method according to claim 23 in which the filter transmittance is computer generated from Mie intensity scattering calculations.

25. A method according to claim 18 in which one of the filters of the set has a uniform transmittance.

26. A method according to claim 18 in which the collected scattering angle range is near backward scattering.

27. A method according to claim 18 in which a polarizing element is placed in the path of the said scattered light.

28. A method according to claim 27 in which the polarizing element is placed ahead of the spatial filters.

29. Apparatus for measurement of the size distribution of particles suspended in a gas or liquid comprising:
- a source of a substantially collimated beam of substantially monochromatic light;
- a lens for collecting a part of the light scattered by the particles, said lens being positioned and oriented such that it does not intersect said beam;
- a set comprising a plurality of spatial filters;
- means to present filters of said set sequentially in an image window located in the focal plane of said lens; and
- a photodetector to produce a sequence of signals each of which is substantially proportional to light transmitted by a respective filter.

30. Apparatus according to claim 29 in which polarizing means is placed in the path of the beam provided by said source.

31. Apparatus according to claim 29 in which polarizing means is placed on the axis of said lens, ahead of said filters.

32. Apparatus according to claim 29 in which the filters are mounted to a rotatable disc.

33. Apparatus according to claim 32 in which means is provided for acting upon said sequence of signals from the photodetector by a linear transformation and using the results as coefficients in a linear combination of basis functions to yield the particle size distribution.

34. Apparatus according to claim 29 in which the filters are comprised of a film strip.

35. Apparatus according to claim 34 in which means is provided for acting upon said sequence of signals from the photodetector by a linear transformation and using the results as coefficients in a linear combination of basis functions to yield the particle size distribution.

36. Apparatus according to claim 29 in which chopper means, synchronized with the presentation of the spatial filter set, intermittently impedes the passage of light to the suspension.

37. Apparatus according to claim 36 in which means is provided for acting upon said sequence of signals from the photodetector by a linear transformation and using the results as coefficients in a linear combination of basis functions to yield the particle size distribution.

38. Apparatus according to claim 29 in which the filters comprise transparencies with a non-uniform transmittance, which at any point P of the filter is a function of the angle $\theta$ which rays that pass through the point P make with the axis of the illuminating beam.

39. Apparatus for measurement of the size distribution of particles suspended in a gas or liquid comprising:
- a source of a substantially collimated beam of substantially monochromatic light;
- a lens for collecting part of the light scattered by the particles;
- a set comprising a plurality of spatial filters;
- means to present filters of said set sequentially in an image window located in the focal plane of said lens;
- a photodetector to produce a sequence of signals each of which is substantially proportional to the light transmitted by a respective filter; and
- means for acting upon said sequence of signals from the photodetector by a linear transformation and using the results as coefficients in a linear combination of basis functions to yield the particle size distribution.

40. Apparatus according to claim 39 in which means is provided for flashing said light source intermittently.

41. Apparatus according to claim 40 in which means is provided for acting upon said sequence of signals from the photodetector by a linear transformation and using the results as coefficients in a linear combination of basis functions to yield the particle size distribution.

42. Apparatus according to claim 39 in which one of the filters of said set has a uniform transmittance, and in which the said last means is so arranged as to subtract the scaled photodetector signal for the uniform filter from the scaled signals for respective non-uniform filters, followed by using the resulting data as coefficients in a linear combination of basis functions.

43. Apparatus according to claim 39 in which polarizing means is placed in the path of the beam provided by said source.

44. Apparatus according to claim 39 in which polarizing means is placed on the axis of said lens, ahead of said filters.

45. A method for measurement of the size distribution of particles suspended in a gas or a liquid, comprising:
- passing a substantially collimated beam of substantially monochromatic light into the particle suspension, said beam having a beam axis;
- with a lens collecting part of the light scattered by the particles, the optical axis of said lens making a non-zero angle with the axis of the illuminating beam;
- sequentially placing the members of a set of spatial filters, one of which has a uniform transmittance, in an image window located in the focal plane of said lens, thereby to transmit light through said set of filters and in the process performing a linear transformation;
- collecting the light transmitted by each of said spatial filters sequentially by a photodetector to produce a signal substantially proportional to light transmitted by respective filters;
- acting on the resulting photodetector sequential signals by a linear transformation; and
- using the resulting data sequence as coefficients in a linear combination of basis functions to yield the particle size distribution.

46. A method according to claim 45 in which said beam is polarized.

47. A method according to claim 45 in which a filter with non-uniform transmittance is provided in said set respective to background light.

* * * * *